(12) United States Patent
Miyazaki et al.

(10) Patent No.: US 8,253,899 B2
(45) Date of Patent: Aug. 28, 2012

(54) BIREFRINGENT FILM

(75) Inventors: Junzo Miyazaki, Ibaraki (JP); Shoichi Matsuda, Ibaraki (JP); Tatsuki Nagatsuka, Ibaraki (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 382 days.

(21) Appl. No.: 12/303,344

(22) PCT Filed: May 17, 2007

(86) PCT No.: PCT/JP2007/060124
§ 371 (c)(1),
(2), (4) Date: Mar. 27, 2009

(87) PCT Pub. No.: WO2007/142003
PCT Pub. Date: Dec. 13, 2007

(65) Prior Publication Data
US 2009/0197065 A1    Aug. 6, 2009

(30) Foreign Application Priority Data
Jun. 8, 2006 (JP) .................. 2006-159579

(51) Int. Cl.
*G02F 1/1335* (2006.01)
(52) U.S. Cl. ........................................ 349/117
(58) Field of Classification Search .............. 428/1.1, 428/1.31; 349/119
See application file for complete search history.

(56) References Cited

U.S. PATENT DOCUMENTS

| 5,635,105 A | 6/1997 | Kawata et al. |
| 2005/0109986 A1* | 5/2005 | Dutova et al. ............ 252/299.01 |
| 2005/0196550 A1* | 9/2005 | Lazarev et al. ................ 428/1.1 |
| 2009/0191394 A1 | 7/2009 | Lazarev et al. |

FOREIGN PATENT DOCUMENTS

| JP | 08-27284 A | 1/1996 |
| JP | 2001-91746 A | 4/2001 |
| JP | 2002-515075 A | 5/2002 |
| JP | 2005-062799 A | 3/2005 |
| JP | 2005-156998 A | 6/2005 |
| JP | 2006-71966 A | 3/2006 |
| JP | 2006-098927 A | 4/2006 |
| JP | 2007-512236 A | 5/2007 |
| JP | 2009-511460 A | 3/2009 |
| WO | 9616015 A1 | 5/1996 |
| WO | 2005/051926 A1 | 6/2005 |

OTHER PUBLICATIONS

Machine Translation of JP 2001-091746.*
International Search Report of PCT/JP2007/060124, date of mailing: Jun. 26, 2007.
Japanese Office Action dated Mar. 23, 2012, issued in corresponding Japanese Patent Application No. 2007-128775 w/Partial English Translation.

* cited by examiner

*Primary Examiner* — Angela Ortiz
*Assistant Examiner* — Anthony J Frost
(74) *Attorney, Agent, or Firm* — Westerman, Hattori, Daniels & Adrian, LLP

(57) ABSTRACT

A birefringent film of the present invention comprises at least one kind of polycyclic compound including a —COOM group (the M denotes a counter ion), wherein an index ellipsoid satisfies a relation of nz>nx=ny. The polycyclic compound includes, for example, acenaphtho[1,2-b]quinoxaline derivative represented by the following general formula (I). The birefringent film of the present invention can be formed thin-type and have a high birefringent index in the thickness direction, since the birefringent film comprises the polycyclic compound.

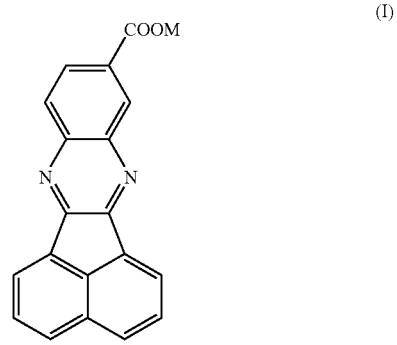

(I)

6 Claims, No Drawings

BIREFRINGENT FILM

TECHNICAL FIELD

The present invention relates to a thin-type birefringent film with a refractive index controlled three-dimensionally, containing at least one kind of polycyclic compound including a —COOM group, a production method thereof and a use thereof.

BACKGROUND ART

A liquid crystal display (also referred to as LCD hereinafter) is an element for displaying characters and images by utilizing electro-optical properties of liquid crystal molecules, and spreads widely in portable telephones, notebook computers, liquid crystal televisions, and the like. However, LCD utilizes liquid crystal molecules having optical anisotropy, so that there is a problem that excellent display properties are exhibited in one direction, while a screen becomes dark and unclear in other directions. A birefringent film is widely provided with LCD to solve such a problem.

A birefringent film such that a refractive index ellipsoid satisfies a relation of nz>nx=ny is known as one of birefringent films (for example, refer to Patent Document 1). The birefringent film having such a relation of the refractive index is produced in such a manner that a homeotropically-aligned side-chain-type liquid crystal polymer is applied on a substrate, subsequently homeotropically aligned in a liquid crystalline state, and solidified while maintaining the aligned state. However, a thinner-type LCD has been earnestly desired from the market. Thus, a thinner-type birefringent film has been demanded.

Patent Document 1: Japanese Unexamined Patent Publication No. 2006-011369

DISCLOSURE OF THE INVENTION

An object of the present invention is to provide a thin-type birefringent film with a refractive index controlled three-dimensionally.

A birefringent film of the present invention comprises at least one kind of polycyclic compound including a —COOM group (the M denotes a counter ion), and an index ellipsoid thereof satisfies a relation of nz>nx=ny.

The birefringent film of the present invention allows a desired retardation value at thin thickness as compared with a conventional birefringent film to be obtained for the reason that the index ellipsoid satisfies a relation of nz>nx=ny and a birefringent index in the thickness direction is high.

In a preferable embodiment of the present invention, a birefringent index (Δn[590]) of the birefringent film at wavelength of 590 nm in the thickness direction is −0.05 or less.

In a preferable embodiment of the present invention, a thickness of the birefringent film is from 0.2 μm to 2.0 μm.

In a preferable embodiment of the present invention, the birefringent film contains acenaphtho[1,2-b]quinoxaline derivative represented by the following general formula (I). The M in the formula (I) denotes a counter ion.

[Formula 1]

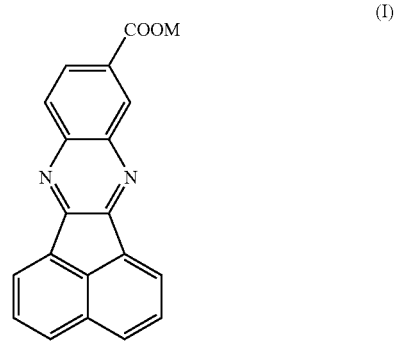

In a preferable embodiment of the present invention, a retardation value (Rth[590]) of the birefringent film at wavelength of 590 nm in the thickness direction is from −300 nm to −10 nm.

In another aspect of the present invention, a laminated film is provided. The laminated film comprises at least the birefringent film and a substrate.

In another aspect of the present invention, a production method of a birefringent film is provided. The production method comprises following steps of (1) to (3):

(1) a step of preparing a solution containing at least one kind of polycyclic compound including a —COOM group (the M denotes a counter ion) and a solvent, and exhibiting a nematic liquid crystalline phase;

(2) a step of preparing a substrate such that at least one surface thereof is hydrophilicly treated; and (3) a step of coating and drying the hydrophilicly treated surface of the substrate prepared in the step of (2) with the solution prepared in the step of (1).

The production method of the birefringent film of the present invention is a method excellent in productivity, such that the film is coated on the substrate and dried, whereby a thin-type birefringent film satisfying a relation of nz>nx=ny can be produced.

In a preferable embodiment of the present invention, the hydrophilizing treatment is at least one kind of treatment including a corona treatment, a plasma treatment, an alkali treatment or an anchor coat treatment.

In a preferable embodiment of the present invention, the substrate is a glass substrate or a polymeric film.

In another aspect of the present invention, a polarizing plate is provided. The polarizing plate comprises at least the birefringent film and a polarizer.

BEST MODE FOR CARRYING OUT THE INVENTION

<1. Outline of Birefringent Film of the Present Invention>

A birefringent film of the present invention comprises at least one kind of polycyclic compound including a —COOM group and an index ellipsoid thereof satisfies a relation of nz>nx=ny. Here, the M denotes a counter ion and the —COOM group denotes a carboxylic acid group or a carboxylate salt.

In the present invention, "birefringent film" denotes a film exhibiting a birefringence in the thickness direction and includes a film exhibiting a birefringent index at wavelength of 590 nm of $1\times10^{-4}$ or more. In the present invention, "nz>nx=ny" denotes an optical anisotropy of a birefringent film when "nx" is determined as an in-plane refractive index in the direction of which an in-plane refractive index is maximum (namely, a slow axis direction), "ny" is determined as an in-plane refractive index in the direction orthogonal to the slow axis direction (namely, a fast axis direction), and "nz" is determined as a refractive index in the thickness direction.

In the present invention, "nx=ny" includes not only the case where nx and ny are completely identical, but also the case where they are substantially identical. Here, "the case where they are substantially identical" denotes, for example, the case where an in-plane retardation value (Re[590]) described below is less than 10 nm.

The above polycyclic compound has two or more of aromatic rings and/or heterocyclic rings, preferably has from 3 to 8 of aromatic rings and/or heterocyclic rings, and more preferably has from 4 to 6 of aromatic rings and/or heterocyclic rings. The use of the polycyclic compound allows a transparent birefringent film having no or little absorption in the visible light region to be obtained.

The birefringent film has an index ellipsoid satisfying a relation of nz>nx=ny and a high birefringent index in the thickness direction, therefore a desired retardation value can be obtained with a small thickness as compared with a conventional birefringent film. According to the presumption of the inventors of the present invention, the reason why the birefringent film of the present invention offers high birefringence is surmised as follows. That is to say, it is conceived that a polycyclic compound including a —COOM group easily forms an aggregate in solution and the order in a state of forming this aggregate is so high that the film formed from the solution also offers high alignment. In the present invention, one of the actions of the —COOM group included in the polycyclic compound on the birefringent film is to improve solubility of the polycyclic compound in a solvent and enable film formation by a solvent casting method, and the other is to control a refractive index three-dimensionally and obtain an index ellipsoid satisfying a relation of nz>nx=ny.

A birefringent index in the thickness direction (Δn[590] =nx−ny) of the birefringent film of the present invention at wavelength of 590 nm is preferably less than −0.05, more preferably from −0.2 to −0.08, and particularly preferably from −0.16 to −0.1. Here, the Δn[590] can be arbitrarily adjusted within the above range by a molecular structure of the polycyclic compound. According to the present invention, the use of the polycyclic compound including the —COOM group first allowed the birefringent film satisfying such a high birefringent index (absolute value) in the thickness direction to be obtained.

A thickness of the birefringent film is preferably from 0.2 μm to 2.0 μm, more preferably from 0.25 μm to 1.8 μm, and particularly preferably from 0.3 μm to 1.7 μm. The use of the polycyclic compound allows the thin-type birefringent film as described in the above to be produced. The use of the birefringent film with such a thickness, for example, as an optical element of a liquid crystal panel is contributable to thinning of a liquid crystal display.

<2. Polycyclic Compound>

With regard to a polycyclic compound used for the present invention, an optional appropriate polycyclic compound may be used if including a —COOM group. The polycyclic compound preferably exhibits a liquid crystalline phase in a solution state (that is, lyotropic liquid crystal). The liquid crystalline phase is preferably a nematic liquid crystalline phase from the viewpoint that alignment is excellent.

The birefringent film preferably contains acenaphtho[1,2-b]quinoxaline derivative represented by the following general formula (I) as the polycyclic compound. In the general formula (I), the M denotes a counter ion.

[Formula 2]

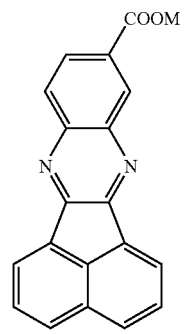

Such a polycyclic compound can form a stable liquid crystalline phase in a solution. A transparent birefringent film having a high birefringent index in the thickness direction and no or little absorption in the visible light region can be produced by performing a solvent casting method for the solution containing the polycyclic compound.

In the above general formula (I), the M denotes a counter ion. The M preferably includes a hydrogen atom, an alkali metal atom, an alkaline earth metal atom, a metal ion, or a substituted or unsubstituted ammonium ion. The metal ion includes, for example, $Ni^{2+}$, $Fe^{3+}$, $Cu^{2+}$, $Ag^+$, $Zn^{2+}$, $Al^{3+}$, $Pd^{2+}$, $Cd^{2+}$, $Sn^{2+}$, $Co^{2+}$, $Mn^{2+}$, $Ce^{3+}$, or the like. For example, in the case where the birefringent film of the present invention is formed from an aqueous solution containing the polycyclic compound and water, with regard to the M described in the above, a group for improving solubility in water may be initially selected and then substituted with a group insoluble or hardly soluble in water after film formation in order to enhance water resistance of the film.

Also, the acenaphtho[1,2-b]quinoxaline derivative described in the general formula (I) can be obtained by condensation reaction of carboxy derivative of benzene-1,2-diamine with acenaphthoquinone as shown in the following reaction formula (a).

[Formula 3]

<3. Physical Properties of Birefringent Film>

A transmittance of the birefringent film at wavelength of 590 nm is preferably 85% or more, and more preferably 90% or more.

A Rth[590] of the birefringent film can be set to be a suitable value within a range in which an index ellipsoid thereof satisfies a relation of nz>nx=ny. The retardation value in the thickness direction (Rth[590]) at wavelength of 590 nm of the birefringent film is from −300 nm to −10 nm, more preferably from −270 nm to −30 nm, and particularly preferably from −250 nm to −50 nm. In the present specification, a retardation value in the thickness direction (Rth[$\lambda$]) denotes a retardation value in the thickness direction at wavelength of $\lambda$ (nm) and at 23° C. The Rth[$\lambda$] can be calculated from the expression of Rth[$\lambda$]=(nx−nz)×d, where a thickness of the film is d (nm).

An in-plane retardation value (Re[590]) at wavelength of 590 nm of the birefringent film is less than 10 nm. In the present specification, an in-plane retardation value (Re[$\lambda$]) denotes an in-plane retardation value at wavelength of $\lambda$ (nm) and at 23° C. The Re[$\lambda$] can be calculated from the expression of Re[$\lambda$]=(nx−ny)×d, where a thickness of the film is d (nm).

A wavelength dispersion value (D) of the birefringent film is preferably 1.01 or more, more preferably from 1.02 to 1.1, and most preferably from 1.03 to 1.07. In the present specification, a wavelength dispersion value (D) denotes a value calculated from the expression of D=R(40)[450]/R(40)[550]. The R(40)[$\lambda$] denotes a retardation value measured at 23° C. and at wavelength of $\lambda$ nm by inclining in a perpendicular direction by 40° with a slow axis of the birefringent film.

In conventional birefringent films, films exhibiting such a steep wavelength dependence were not obtained. With regard to the birefringent film of the present invention, a retardation value measured by light with short wavelength is sufficiently larger than a retardation value measured by light with long wavelength. Thus, the characteristic of the birefringent film of the present invention is also to exhibit steep wavelength dependence of retardation.

<4. Production Method of Birefringent Film>

In one embodiment, a birefringent film of the present invention is produced by the method including the following step (1) to step (3).

(1) a step of preparing a solution containing at least one kind of polycyclic compound including a —COOM group (the M denotes a counter ion) and a solvent, and exhibiting a nematic liquid crystalline phase, (2) a step of preparing a substrate such that at least one surface thereof is hydrophilicly treated, and (3) a step of coating and drying the hydrophilicly treated surface of the substrate prepared in the step of (2) with the solution prepared in the step of (1).

Such a production method allows a laminated film provided with at least a birefringent film and a substrate to be obtained.

The polycyclic compound including a —COOM group (the M denotes a counter ion) used in the step (1) may be selected from the above arbitrarily and appropriately. Preferable examples of the polycyclic compound include the acenaphtho[1,2-b]quinoxaline derivative represented by the above general formula (I).

The solvent is used for dissolving the polycyclic compound to develop a nematic liquid crystalline phase. The solvent may be selected optionally and appropriately. The solvent may be an inorganic solvent such as water or an organic solvent. With regard to the organic solvent, alcohol, ketone, ether, ester, aliphatic hydrocarbon, aromatic hydrocarbon, halogenated carbon hydride, amide, cellosolve, and the like may be used. Specifically, the organic solvent is, for example, n-butanol, 2-butanol, cyclohexanol, isopropyl alcohol, t-butyl alcohol, glycerin, ethylene glycol, acetone, methylethylketone, cyclohexane, cyclopentanone, 2-pentanone, 2-hexanone, diethyl ether, tetrahydrofuran, dioxane, anisole, acetic ether, butyl acetate, methyl lactate, n-hexane, benzene, toluene, xylene, chloroform, dichloromethane, dichloroethane, dimethylformaldehyde, dimethylacetamide, methylcellosolve, ethylcellosolve, and the like. The solvent is used singly or in combination of two kinds or more.

The solvent is particularly preferably water. Electric conductivity of water is preferably 20 $\mu$S/cm or less, more preferably from 0.001 $\mu$S/cm to 10 $\mu$S/cm, and particularly preferably from 0.01 $\mu$S/cm to 5 $\mu$S/cm. The lower limit of the electric conductivity of water is 0 $\mu$S/cm. By use of water in which the electric conductivity is within the above range, a birefringent film having a high birefringent index in the thickness direction may be obtained.

A concentration of the polycyclic compound in the solution is prepared optionally and appropriately range depended on the kind of the polycyclic compound if exhibiting a nematic liquid crystalline phase. The concentration of the polycyclic compound in the solution is preferably from 5% to 30% by weight, more preferably 7% to 20% by weight, and particularly preferably from 9% to 15% by weight. The solution may form a stable liquid crystalline state by determining the concentration of the solution at the range. The nematic liquid crystalline phase can be confirmed and distinguished by an optical pattern of the liquid crystalline phase observed with a polarizing microscope.

Further, into the solution, an additive may be added optionally and appropriately. Examples of the additive include a surfactant, a plasticizer, a thermal stabilizer, an optical stabilizer, a lubricant, an antioxidant, an ultraviolet absorber, a flame retardant, a coloring agent, an antistatic agent, a compatibility improving agent, a cross-linking agent, a thickening agent, and the like. The additive amount of these additives is preferably more than 0 and 10 or less parts by weight relative to 100 parts by weight of the solution.

"Hydrophilizing treatment" in the step (2) denotes a treatment for decreasing a contact angle of water on the substrate. The hydrophilizing treatment is performed for improving wettability and coatability of the substrate surface coated with the polycyclic compound. The hydrophilizing treatment is a treatment for decreasing a contact angle of water on the substrate at a temperature of 23° C. preferably by 10% or more, more preferably by from 15% to 80% and particularly preferably by from 20% to 70% as compared with a state before the treatment. This decreasing ratio (%) is calculated from the expression: {(contact angle before treatment−contact angle after treatment)/contact angle before treatment}× 100.

In addition, the hydrophilizing treatment is a treatment for decreasing the contact angle of water on the substrate at a temperature of 23° C. preferably by 5° or more, more preferably by from 10° to 65°, and particularly preferably by from 20° to 65° as compared with a state before the treatment.

The above hydrophilizing treatment is a treatment for setting the contact angle of water on the substrate at a temperature of 23° C. preferably by from 5° to 60°, more preferably by from 5° to 50°, and particularly preferably by from 5° to 45°. By setting the contact angle of water on the substrate within the above range, a birefringent film having a high birefringent index in the thickness direction and narrow thickness dispersion may be obtained.

The hydrophilizing treatment can be any appropriate method. For example, the hydrophilizing treatment may be a dry treatment or a wet treatment. The dry treatment includes, for example, a discharge treatment such as a corona treatment, a plasma treatment, or a glow discharge treatment; a flame treatment; an ozone treatment; an UV ozone treatment; an ionization active ray treatment such as an ultraviolet treatment or an electron beam treatment; and the like. The wet treatment includes, for example, an ultrasonic treatment using a solvent such as water or acetone; an alkali treatment; an anchor coat treatment; and the like. The treatment can be used singly or in combination of two kinds or more.

The hydrophilizing treatment is preferably the corona treatment, the plasma treatment, the alkali treatment, or the anchor coat treatment. The use of these treatments allows a birefringent film having a high alignment and narrow thickness dispersion to be obtained. With regard to the condition of the hydrophilizing treatment (for example, treating time or intensity), it can be set to be a suitable and appropriate value as far as the contact angle of water on the substrate is within the above range.

The corona treatment is typically a treatment for modifying the substrate surface by passing the substrate through corona discharge. The corona discharge is caused in such a manner that air between the electrodes is subjected to dielectric breakdown and ionized by impressing high frequency and high voltage between a grounded dielectric roll and an insulated electrode. The plasma treatment is typically a treatment for modifying the substrate surface by passing the substrate through low-temperature plasma. The low-temperature plasma is caused in such a manner that glow discharge is caused in inorganic gases such as low-pressure inert gas, oxygen gas and halogen gas, and then a part of the gaseous molecules are ionized. The ultrasonic treatment is typically a treatment for removing contaminations on the substrate and improving wettability thereof. The ultrasonic treatment is performed such that the substrate is immersed in water and an organic solvent and irradiated with ultrasonic waves. The alkali treatment is typically a treatment for modifying the substrate surface by immersing the substrate in an alkali treatment solution such that a basic material is dissolved in water or an organic solvent. The anchor coat treatment is typically a treatment for coating the substrate surface with an anchor coat agent.

The substrate of the present invention is used for uniformly developing the above solution containing the polycyclic compound and the solvent. The substrate may be selected optionally and appropriately. The substrate is, for example, a glass substrate, a quartz substrate, a polymeric film, a plastic substrate, a metal substrate made of aluminum or iron, a ceramic substrate, a silicon wafer, and the like. The substrate is preferably the glass substrate or the polymeric film.

The glass substrate may be selected optionally and appropriately. The glass substrate is preferably used for a liquid crystal cell. Examples of the glass substrate used for the liquid crystal cell include soda-lime glass (blue sheet) containing an alkaline component, low-alkali borax acid glass, or the like. A commercial glass substrate may be directly used for the glass substrate. Examples of the commercial glass substrate include glass code: 1373 manufactured by Corning Incorporated, glass code: AN635 manufactured by Asahi Glass Co., Ltd. and glass code: NA-35 manufactured by NH Techno Glass Corporation.

A resin forming the polymeric film may be selected optionally and appropriately. The polymeric film preferably contains a thermoplastic resin. The thermoplastic resin includes, for example, a polyolefin-based resin, a cycloolefin-based resin, polyvinyl chloride-based resin, a cellulose-based resin, a styrene-based resin, a polymethylmethacrylate, a polyvinyl acetate, a polyvinylidene chloride-based resin, a polyamide-based resin, a polyacetal-based resin, a polycarbonate-based resin, a polybutylene terephthalate-based resin, a polyethylene terephthalate-based resin, a polysulphone-based resin, a polyether sulphone-based resin, a polyether ether ketone-based resin, a polyarylate-based resin, a polyamide-imide-based resin, and the like. The thermoplastic resin is used singly or in combination of two kinds or more. The thermoplastic resin may be also used after performing optional and appropriate polymer modification. Examples of the polymer modification include copolymerization, crosslinking, molecular ends and stereoregularity.

The substrate of the present invention is preferably a polymeric film containing a cellulose-based resin. The substrate containing the cellulose-based resin is excellent in wettability of the polycyclic compound, therefore a birefringent film having a high birefringent index in the thickness direction and narrow thickness dispersion may be obtained.

The cellulose-based resin may be used optionally and appropriately. The cellulose-based resin is preferably a cellulose organic acid ester or a cellulose mixed organic acid ester, in which a part or all of hydroxyl groups of the cellulose are substituted with acetyl groups, propionyl groups and/or butyl groups. Examples of the cellulose organic acid ester include cellulose acetate, cellulose propionate, cellulose butyrate, and the like. Examples of the cellulose mixed organic acid ester include cellulose acetate propionate, cellulose acetate butyrate, and the like. The cellulose-based resin may be obtained by the method described in [0040] and [0041] of Japanese Unexamined Patent Publication No. 2001-188128, for example.

A commercial polymeric film may be also directly used for the substrate of the present invention. Alternatively, a commercial polymeric film for which secondary elaborations such as a drawing treatment and/or a contraction treatment are performed may be also used. Examples of the commercial polymeric film containing a cellulose-based resin include FUJITAC series (trade name: ZRF80S, TD80UF, and TDY-80UL) manufactured by Fuji Photo Film Co., Ltd. and trade name "KC8UX2M" manufactured by Konica Minolta Opt, Inc.

A thickness of the substrate is preferably from 20 µm to 100 µm. Handling ability and coatability of the substrate become excellent by determining the thickness of the substrate within the above range.

A coating rate of the solution in the step (3) is preferably 50 mm/second or more, and more preferably 100 mm/second or more. A birefringent film with narrow thickness dispersion, having a high birefringent index in the thickness direction, may be obtained by determining the coating rate within the above range.

With regard to a method of coating the solution, a coating method using an optional appropriate coater may be used. The coater includes, for example, a reverse roll coater, a positive rotation roll coater, a gravure roll coater, a knife coater, a rod coater, a slot die coater, a slot orifice coater, a curtain coater, a fountain coater, an air doctor coater, a kiss coater, a dip coater, a bead coater, a blade coater, a cast coater, a spray coater, a spin coater, an extrusion coater, a hot-melt coater, and the like. The coater is preferably the reverse roll coater, the positive rotation roll coater, the gravure roll coater, the rod coater, the slot die coater, the slot orifice coater, the curtain coater, and the fountain coater.

With regard to a method of drying the solution, an optional appropriate method may be used. The drying method includes, for example, an air-circulation thermostat oven in which hot air or cold air is circulated, a heater using a microwave, a far infrared ray, or the like, a roll heated for temperature regulation, a heated heat pipe roll, a heated metal belt, or the like.

The temperature for drying the solution is below or equal to the isotropic phase transition temperature of the solution, and the temperature is preferably raised gradually from a low temperature to a high temperature. The above drying temperature is preferably from 10° C. to 80° C., and more preferably from 20° C. to 60° C. Within such a temperature range, a birefringent film having narrow thickness dispersion can be obtained.

The period of time for drying the solution can be selected arbitrarily and appropriately depending on the drying temperature and the kind of the solvent. In order to obtain a birefringent film having narrow thickness dispersion, the drying time is, for example, from 1 minute to 30 minutes, and preferably from 1 minute to 10 minutes. By drying the solution, a laminated body (laminated film) of which a birefringent film is laminated on the surface of the substrate is obtained.

A production method of the birefringent film of the present invention preferably comprises a step (4) in addition after the above step (1) to (3).

(4) a step of bringing the birefringent film obtained in the above step (3) into contact with a solution containing at least one kind of a compound salt selected from the group consisting of aluminum salt, barium salt, lead salt, chromium salt, strontium salt, and compound salts having two or more amino groups within a molecule.

In the present invention, the step (4) is performed for imparting water resistance to the obtained birefringent film. The compound salt includes, for example, aluminum chloride, barium chloride, lead chloride, chromium chloride, strontium chloride, 4,4'-tetramethyldiaminophenylmethane hydrochloride, 2,2'-dipyridyl hydrochloride, 4,4'-dipyridyl hydrochloride, melamine hydrochloride, tetraaminopyrimidine hydrochloride, and the like. These compound salts allow a birefringent film excellent in water resistance to be obtained.

In the solution containing the above compound salt, the concentration of the compound salt is preferably from 3 to 40% by weight, and particularly preferably from 5% to 30% by weight. By bringing the birefringent film into contact with the solution containing the compound salt in the above range, a birefringent film excellent in durability can be obtained.

As a method of bringing the birefringent film obtained in the above step (3) into contact with the solution containing the above compound salt, optional one can be used, for example, (i) a method of coating the solution containing the above compound salt onto the surface of the birefringent film, (ii) a method of immersing the birefringent film into the solution containing the above compound salt, or the like. In the case that these methods are used, a obtained birefringent film is preferably washed with water or an arbitrary solvent for removing a residual solution (a solution containing the compound salt). In addition, a laminated body excellent in adhesion properties of the interface between the substrate and the birefringent film may be obtained by drying this.

<5. Use of Birefringent Film>

A birefringent film of the present invention is not used for particularly limited uses. Examples of typical uses include a λ/4 plate, a λ/2 plate and a view angle widening film of a liquid crystal display, and an antireflection film for flat panel displays. In one embodiment of the present invention, the birefringent film may be laminated a polarizer and used as a polarizing plate. Hereinafter, the polarizing plate will be described.

<6. Polarizing Plate of the Present Invention>

A polarizing plate of the present invention comprises at least the above birefringent film and a polarizer. The polarizing plate may further include a laminated film at least comprising the birefringent film and a substrate. The polarizing plate may further include an other birefringent film or an arbitrary protective layer. Practically, an optional appropriate adhesive layer is provided between each of the component elements that make up the polarizing plate, and the polarizer and the each component elements are adhered.

The above polarizer is not limited and any optional one may be used as far as the polarizer converts natural light or polarized light into linearly polarized light. The polarizer is preferably a drawn film having as the main component polyvinyl alcohol resin containing iodine or dichromatic dye. In general, a thickness of the polarizer is from 5 μm to 50 μm.

The adhesive layer can be selected from any optional one as far as the adhesive layer joins planes of adjacent elements, which are integrated by practically sufficient adhesive force and adhesive time. Examples of a material for forming the adhesive layer include an adhesive agent, a pressure-sensitive agent, and an anchor coat agent. The adhesive layer may be a multi-layered structure such that an anchor coat layer is formed on the surface of an adherend to form an adhesive agent layer or a pressure-sensitive agent layer thereon, or a thin layer unrecognizable with the naked eye (also referred to as hairline). The adhesive layer disposed on one side of the polarizer and the adhesive layer arranged on the other side thereof may be the same or different.

EXAMPLES

The present invention will be further described by showing Examples. However, it is to be noted that the present invention is not limited to these Examples. Here, measuring methods used in Examples are as follows.

(1) Measurement method of thickness:

In the case of being less than 10 μm, a thickness was measured by using a spectrophotometer for thin films [trade name "Multi Channel Photo Detector MCPD-2000", manufactured by Otsuka Electronics Co., Ltd.]. In the case of being 10 μm or more, a thickness was measured by using a digital micrometer "KC-351C", manufactured by Anritsu Corporation.

(2) Measuring method of transmittance (T[590]), birefringent index in the thickness direction (Δn[590]), retardation value (Re[λ], Rth[λ]), wavelength dispersion value (D) (R(40) [450]/R(40) [550]):

These were measured by using "KOBRA21-ADH" (trade name) manufactured by Oji Scientific Instruments at 23° C. For average refractive index, values measured using an Abbe refractometer [trade name "DR-M4" manufactured by ATAGO Co., Ltd.] were used.

(3) Measuring method of electric conductivity:

After an electrode of a solution electric conductivity meter [trade name "CM-117", manufactured by Kyoto Electronics Manufacturing Co., Ltd.] was washed in an aqueous solution in which the concentration was prepared at 0.05% by weight, a sample was filled into a 1-cm$^3$ container connected to the electrode and the displayed electric conductivity showed a constant value, which was regarded as a measured value.

(4) Measuring method of contact angle of water:

After liquid was dropped onto a substrate by using a solid-liquid interface analyzer [trade name "Drop Master 300", manufactured by Kyowa Interface Science Co., Ltd.], a contact angle after 5 seconds was measured. The measurement condition was static contact angle measurement. Ultrapure water was used for water and droplets were 0.5 μl. With regard to each substrate, the average value through ten repeated times was regarded as a measured value.

Synthesis Example 1

<Synthesis of acenaphtho[1,2-b] quinoxaline-9-carboxylic acid>

500 mL of dimethylformaldehyde was added to a mixture of 10 g of purified acenaphthenequinone and 84 g of 3,4-diaminobenzoic acid. The reactant continued to be stirred at room temperature for 21 hours. The precipitate was filtered to obtain a crude composition. This crude composition was dissolved in heated dimethylformamide, filtered again and purified by washing in dimethylformamide and water.

Synthesis Example 2

<Synthesis of acenaphtho [1,2-b] quinoxaline-9-ammonium Carboxylate>

As shown in the following reaction path (b), the purified acenaphtho[1,2-b]quinoxaline-9-carboxylic acid was dissolved in 2-liter pure water (electric conductivity: 1.7 μS/cm) to further add ammonium hydroxide thereto, with which the acid was neutralized. The obtained aqueous solution was put in a feed tank and purified by using triple flat film evaluation equipment provided with a reverse osmosis film filter (trade name "NTR-7430") manufactured by Nitto Denko Corp. Next, this purified aqueous solution was adjusted by using a rotary evaporator so that the concentration of the polycyclic compound in the aqueous solution became 13.3% by weight. When the aqueous solution thus obtained was observed with a polarizing microscope, the aqueous solution offered a nematic liquid crystalline phase at a temperature of 23° C.

[Formula 4]

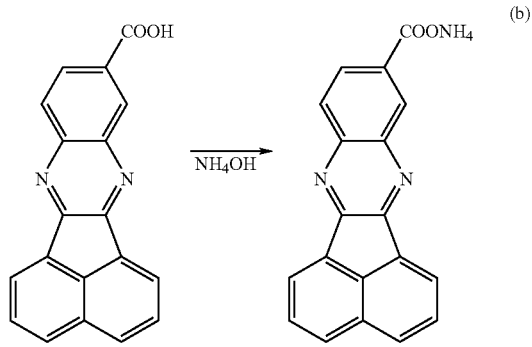

(b)

Example 1

A polymeric film [trade name "ZRF80S", manufactured by Fuji Photo Film Co., Ltd.] having 80-λm-thickness triacetyl cellulose as the main component was immersed in an aqueous solution, in which sodium hydroxide was dissolved, to perform alkali treatment (also called saponification treatment) on the surface thereof. The contact angle of water of the polymeric film at a temperature of 23° C. was 64.6° before the treatment and 26.5° after the treatment. Next, the alkali-treated surface of the polymeric film was coated with the aqueous solution obtained in the Synthesis Example 2 by using a bar coater [trade name "mayor rot HS1.5", manufactured by Buschman Corp.] so that the thickness after drying became 0.35 μm. The coated film was dried in a thermostatic chamber at a temperature of 23° C. while blowing on the coated surface, and thereafter further dried in an air-circulating drying oven at a temperature of 40° C. for 3 minutes. As a result, a birefringent film A such that an index ellipsoid exhibits a relation of nz>nx=ny was formed on the surface of the polymeric film having triacetyl cellulose as the main component. The characteristics of this birefringent film A are shown in Table 1.

TABLE 1

| | Birefringent films | | | | | |
|---|---|---|---|---|---|---|
| | A | B | C | D | E | F |
| Thickness (μm) | 0.35 | 0.45 | 0.61 | 0.85 | 1.5 | 1.6 |
| Δn [590] | −0.15 | −0.14 | −0.14 | −0.13 | −0.11 | −0.15 |
| T [590] (%) | 90 | 90 | 90 | 90 | 90 | 90 |
| Rth [590] (nm) | −53 | −65 | −85 | −110 | −160 | −240 |
| Re [590] (nm) | 0.1 | 0.1 | 0.1 | 0.1 | 0.1 | 0.1 |
| R (40) [450]/R (40) [550] | 1.05 | 1.05 | 1.05 | 1.05 | 1.05 | 1.05 |

Example 2

A birefringent film B exhibiting a relation of nz>nx=ny was obtained in the same manner as Example 1 except for coating with the aqueous solution obtained in the Synthesis Example 2 so that a thickness after drying became 0.45 μm. The characteristics of this birefringent film B are shown in Table 1.

Example 3

A birefringent film C exhibiting a relation of nz>nx=ny was obtained in the same manner as Example 1 except for coating with the aqueous solution obtained in the Synthesis Example 2 so that a thickness after drying became 0.61 μm. The characteristics of this birefringent film C are shown in Table 1.

Example 4

A birefringent film D exhibiting a relation of nz>nx=ny was obtained in the same manner as Example 1 except for coating with the aqueous solution obtained in the Synthesis Example 2 so that a thickness after drying became 0.85 μm. The characteristics of this birefringent film D are shown in Table 1.

Example 5

A birefringent film E exhibiting a relation of nz>nx=ny was obtained in the same manner as Example 1 except for coating with the aqueous solution obtained in the Synthesis Example 2 so that a thickness after drying became 1.5 μm. The characteristics of this birefringent film E are shown in Table 1.

Example 6

A birefringent film F exhibiting a relation of nz>nx=ny was obtained in the same manner as Example 1 except for coating with the aqueous solution obtained in the Synthesis Example 2 so that a thickness after drying became 1.6 μm. The characteristics of this birefringent film F are shown in Table 1.

Evaluation

As shown in Examples 1 to 5, a birefringent film offering a high birefringent index in the thickness direction, such that an index ellipsoid satisfies a relation of nz>nx=ny, can be obtained by coating a substrate surface with solution containing at least a polycyclic compound including a —COOM group and a solvent. These birefringent films allow a predetermined retardation value at a thin thickness as compared with conventional birefringent films to be obtained.

As described above, the birefringent film of the present invention satisfies a relation of nz>nx=ny and exhibits a high birefringent index in the thickness direction; therefore, for example, in the case of being used for a liquid crystal display, the birefringent film can greatly contribute to improvement in display properties and thinning.

What is claimed is:

1. A birefringent film, comprising: at least one kind of polycyclic compound including a —COOM group;

wherein an index ellipsoid of the birefringent film satisfies a relation of nz>nx=ny, and the polycyclic compound contains acenaphtho[1,2-b]quinoxaline derivative represented by the following general formula (I),

[Formula I]

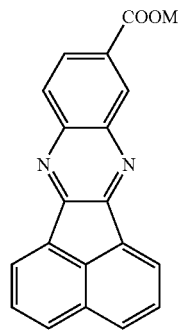

wherein M in formula (I) denotes a counter ion.

2. The birefringent film according to claim 1, wherein a birefringent index (Δn[590]) of the birefringent film at wavelength of 590 nm in the thickness direction is −0.05 or less.

3. The birefringent film according to claim 1, wherein a thickness of the birefringent film is from 0.2 μm to 2.0 μm.

4. The birefringent film according to claim 1, wherein a retardation value (Rth[590]) of the birefringent film at wavelength of 590 nm in the thickness direction is from −300 nm to −10 nm.

5. A laminated film comprising at least the birefringent film according to claim 1 and a substrate.

6. A polarizing plate comprising at least the birefringent film according to claim 1 and a polarizer.

* * * * *